(12) United States Patent
Boyd et al.

(10) Patent No.: US 9,358,342 B2
(45) Date of Patent: Jun. 7, 2016

(54) FLEXIBLE RESERVOIR FOR A MEDICATED MODULE

(75) Inventors: Malcolm Stanley Boyd, Wellesbourne (GB); James Alexander Davies, Leamington Spa (GB); Andrew Gordon Wallace, Highleadon (GB); David Sanders, Warwick (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 967 days.

(21) Appl. No.: 13/519,793

(22) PCT Filed: Feb. 1, 2011

(86) PCT No.: PCT/EP2011/051393
§ 371 (c)(1),
(2), (4) Date: Oct. 4, 2012

(87) PCT Pub. No.: WO2011/095478
PCT Pub. Date: Aug. 11, 2011

(65) Prior Publication Data
US 2013/0018323 A1     Jan. 17, 2013

Related U.S. Application Data

(60) Provisional application No. 61/301,703, filed on Feb. 5, 2010.

(30) Foreign Application Priority Data

Apr. 23, 2010 (EP) ..................................... 10160836

(51) Int. Cl.
*A61J 1/22* (2006.01)
*A61M 5/32* (2006.01)
(Continued)

(52) U.S. Cl.
CPC ............. *A61M 5/284* (2013.01); *A61M 5/2448* (2013.01); *A61M 5/326* (2013.01); *A61M 5/2425* (2013.01);
(Continued)

(58) Field of Classification Search
CPC .................. A61M 2005/3267; A61M 5/3294; A61M 5/3297; A61M 5/347; A61M 2005/1787; A61M 5/3155; A61M 5/2448; A61M 5/284; A61M 5/326; A61M 5/2425; A61M 5/3146; A61M 5/31525
See application file for complete search history.

(56) References Cited

U.S. PATENT DOCUMENTS 2,674,246 A * 4/1954 Bower .......................... 604/198
3,892,237 A    7/1975 Steiner
(Continued)

FOREIGN PATENT DOCUMENTS

JP    2002537030 A    11/2002
JP    2002542903       12/2002
(Continued)

OTHER PUBLICATIONS

English Translation of Notice of Reasons for Rejection Mailed in Japanese Patent Application No. 2012-551593 dated Oct. 21, 2014.
(Continued)

*Primary Examiner* — Theodore Stigell
(74) *Attorney, Agent, or Firm* — McDonnell Boehnen Hulbert & Berghoff LLP (57) ABSTRACT

A reservoir (31) with at least one flexible section for use in a medicated module (4) for an injection system to co-deliver at least two medicaments is disclosed where a primary delivery device (7) containing a first medicament accepts a medicated module (4) containing a single dose of a second medicament (2) and where both medicaments are delivered through a single hollow needle (3). The reservoir (31) comprises one or more slit valves (44, 45) to allow for delivery of the first and second medicaments. The medicated module (4) also contains a needle guard (22) that engages a housing (43) of the reservoir (31) to open the slit valves (44, 45).

17 Claims, 2 Drawing Sheets

(51) Int. Cl.
  *A61M 5/31* (2006.01)
  *A61M 5/28* (2006.01)
  *A61M 5/24* (2006.01)
  *A61M 5/315* (2006.01)
  *A61M 5/34* (2006.01)
  *A61M 5/178* (2006.01)

(52) U.S. Cl.
  CPC .............. *A61M 5/282* (2013.01); *A61M 5/3146* (2013.01); *A61M 5/3155* (2013.01); *A61M 5/31525* (2013.01); *A61M 5/3294* (2013.01); *A61M 5/3297* (2013.01); *A61M 5/347* (2013.01); *A61M 2005/1787* (2013.01); *A61M 2005/3267* (2013.01)

(56) References Cited

U.S. PATENT DOCUMENTS

| | | | |
|---|---|---|---|
| 6,527,738 B1 * | 3/2003 | Jones et al. | 604/84 |
| 6,562,002 B1 | 5/2003 | Taylor | |
| 2002/0091361 A1 * | 7/2002 | Rosoff et al. | 604/212 |
| 2006/0276755 A1 | 12/2006 | Sullivan et al. | |

FOREIGN PATENT DOCUMENTS

| | | |
|---|---|---|
| JP | 2004173836 A | 6/2004 |
| JP | 2004522519 A | 7/2004 |
| WO | 0066214 A1 | 11/2000 |
| WO | 02060517 A2 | 8/2002 |
| WO | 2007026163 A1 | 3/2007 |

OTHER PUBLICATIONS

International Preliminary Report on Patentability for Int. App. No. PCT/EP2011/051393, mailed Aug. 16, 2012.

English Translation of Notice of Reasons for Rejection issued in Japanese Patent Application No. 2012-551593 dated Jul. 14, 2015.

* cited by examiner

FLEXIBLE RESERVOIR FOR A MEDICATED MODULE

CROSS REFERENCE TO RELATED APPLICATIONS

The present application is a 35 U.S.C. 371 National Application of PCT/EP2011/051393 filed Feb. 1, 2011, which claims priority to U.S. Provisional Patent Application No. 61/301,703 filed Feb. 2, 2010 and European Patent Application No. 10160836.2 filed Apr. 23, 2010, the entire contents of which are incorporated entirely herein by reference.

FIELD OF THE PRESENT PATENT DISCLOSURE

Specific embodiments of this disclosure relate to medical devices and methods of delivering at least two drug agents from separate reservoirs using devices having only a single dose setting mechanism and a single dispense interface. A single delivery procedure initiated by the user causes a, preferably, non-user settable dose of a second drug agent and a, preferably, variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our disclosure concerns a flexible reservoir containing a single dose of a second medicament. The reservoir can be used in a medicated module that is attachable to a primary drug delivery device. At least one slit valve (in particular "camelback" type valve) may allow the second medicament to be dispensed from the flexible reservoir. This may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or cognitive difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The above-mentioned problems may be overcome by providing separate storage containers for two or more active drug agents that are then only combined and/or delivered to the patient during a single delivery procedure. Setting a dose of one medicament may automatically fix or determine the dose of the second medicament (i.e. non-user settable). Moreover, the opportunity may be given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Our disclosure also provides a flexible reservoir for use in a medicated module that contains a single dose of a second medicament. The flexible housing of the reservoir may be characterized by having at least one valve, preferably a slit valve, to allow for a bypass of primary medicament during a priming step and/or to dispense the single dose of the second medicament. A needle guard may be included that interacts with the flexible reservoir housing to open the valve.

These and other advantages will become evident from the following more detailed description of the invention.

Problem to be Solved

The problem to be solved by the present invention is to provide a reservoir, a medicated module and a drug delivery device where the administration of a medicament is improved.

SUMMARY

The disclosed reservoir, medicated module and drug delivery device may allow complex combinations of multiple drug compounds within a single drug delivery system. In particular, the user may be enabled to set and dispense a multi-drug compound device through one single dose setting mechanism and a single dispense interface. This single dose setter expediently controls the mechanism of the device such that a predefined combination of the individual drug compounds is delivered when a single dose of one of the medicaments is set and dispensed through the single dispense interface.

By defining the therapeutic relationship between the individual drug compounds our delivery device may help to ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

The disclosed reservoir, medicated module and drug delivery device may be of particular benefit to users with dexterity or cognitive difficulties as the single input and associated predefined therapeutic profile removes the need for them to calculate their prescribed dose every time they use the device and the single input allows considerably easier setting and dispensing of the combined compounds.

In a preferred embodiment a master drug compound, such as insulin, contained within a multiple dose, user selectable device could be used with a single use, user replaceable, module that contains a single dose of a second medicament and the single dispense interface. When connected to the primary device the second compound is activated/delivered on dispense of the primary compound. Although this disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the present disclosure.

The term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to one aspect, a reservoir for use in a medicated module is provided. The medicated module may be, preferably releasably, attachable to a drug delivery device. The reservoir may comprise a flexible housing. Alternatively, the reservoir may comprise a housing having at least one flexible section. In this case, the housing may also comprise less flexible or rigid sections. The at least partly flexible housing may define an interior chamber. The housing of the reservoir may comprise a proximal end and a distal end. The reservoir may comprise an end cap. The end cap may be less flexible than the housing, in particular less flexible than the flexible section of the housing. The end cap may be rigid. In particular, the end cap may be constructed using a material more rigid than the material used to manufacture the at least one flexible section of the housing. The end cap may be located at the proximal end of the housing. Accordingly, the interior chamber, preferably the proximal end of the interior chamber, may be sealed with the end cap. The reservoir may comprise a valve. The reservoir and the valve may be integrally formed. The valve may be arranged in the at least one flexible section of the housing. In particular, the area around the valve may be flexible. The valve may be a flexible valve. The valve is expediently located at the distal end of the flexible housing.

The flexible or at least partly flexible housing may be manufactured using medical grade of silicon, thermoplastic elastomers, or like materials, provided that the material of construction is compatible with the medicament contained in the reservoir.

A further aspect relates to a medicated module. The medicated module may be, preferably releasably, attachable to a drug delivery device. Said drug delivery device may comprise a primary reservoir holding at least one dose, preferably a plurality of doses, of a first medicament. The medicated module may comprise a second medicament, preferably a single dose of the second medicament. The second medicament may be retained in the interior chamber of the previously described reservoir. The medicated module may be a medicated needle. The medicated module may comprise a first or distal needle cannula. The medicated module may comprise a second or proximal needle cannula. The reservoir of the medicated module may be arranged in the axial direction between the first and the second needle cannula. The needle cannulae may be configured for establishing fluid communication with the reservoir. The distal end of the distal needle cannula may be configured for being applied to an injection site. The proximal end of the distal needle cannula may be configured for piercing the reservoir, in particular a seal or septum arranged at the distal end of the reservoir. The distal end of the proximal needle cannula may be configured for piercing the reservoir, in particular a seal or septum arranged at the proximal end of the reservoir. The proximal end of the proximal needle may be configured for piercing the primary reservoir, in particular a seal or septum arranged at the distal end of the primary reservoir. The medicated module, in particular the reservoir of the medicated module, may be pre-filled with the second medicament when the medicated module is attached to the device, in particular before fluid communication is established between the secondary reservoir and at least one of the first and the second needle cannula. The drug delivery device, in particular the primary reservoir, may be at least partly filled with first medicament before the module is attached to the device.

The drug delivery device may be suitable to set and dispense a dose of the first medicament before the medicated module is attached to the device or after the medicated module was removed from the device. Accordingly, the device may be suitable to form a stand-alone device, configured to operate also in absence of the medicated module, for example. For this purpose, a needle cannula may be, preferably removably, attachable to the distal end of the device.

The medicated module may comprise a housing. The housing may have a distal end and a proximal end. The housing may be configured for attachment to the drug delivery device. The housing, preferably the proximal end of the housing, may have a connector. The connector may be configured for attachment to the drug delivery device. The previously described reservoir is expediently arranged in a portion of the housing. The medicated module may comprise a guard, in particular a needle guard. The needle guard may be operably connected to the housing. The needle guard may be adapted and arranged to provide protection against the needle cannula arranged in a portion of the medicated module. The needle guard may be configured to move in an axial direction during application to an injection site. The needle guard may be configured to engage the flexible or at least partly flexible housing of the medicated module.

The rigid end cap of the reservoir may provide a liquid seal between the second medicament and the outside of the interior chamber. The rigid end cap may comprise a valve. Said valve may comprise a check or duck valve. The check or duck valve may be in fluid communication with the interior chamber and, in particular, with the second medicament.

The valve, which may be arranged at the distal end of the reservoir, may be a slit valve, e.g. a camelback type valve. The slit valve may be in fluid communication with the interior chamber and, in particular, with the second medicament held in the interior chamber. During injection, in particular when the previously mentioned needle guard is moved in an axial, in particular the proximal, direction, e.g. when the needle guard is retracted, this slit valve is forced, e.g. squeezed, to an open position due to mechanical cooperation of the at least partly flexible housing and the needle guard. In particular, squeezing the valve open may be enabled by the flexible section of the housing in which the valve is arranged. In particular, upon retraction of the needle guard, mechanical cooperation of the needle guard and the housing, in particular mechanical cooperation of the needle guard and the flexible section of the housing, may cause the slit valve arranged at the distal end of the reservoir to squeeze open, thus allowing the second medicament to flow out of the interior chamber. Once the distally arranged valve is opened, the hydraulic pressure within the reservoir is reduced on the distal portion of the proximally arranged valve, i.e. the valve of the rigid end cap. The pressure of the first medicament exerted on the proximal side of the rigid end cap and the proximal portion of valve of the rigid end cap may cause the valve of the rigid end cap to be forced open allowing a set dose of first medicament to flow into the interior chamber of the reservoir, thus driving or forcing out the second medicament.

According to an embodiment, the flexible or at least partly flexible housing comprises a, preferably radial, protrusion. The protrusion may be arranged on an outer surface of the flexible housing. The, preferably radial, protrusion may be operably connected to the valve. Mechanical cooperation of the flexible or at least partly flexible housing of the reservoir, in particular of the protrusion, and the needle guard may enable opening of the valve of the reservoir.

According to an embodiment, the reservoir comprises a bypass channel. The bypass channel may comprise a fluid path bypassing the reservoir of the medicated module. The bypass channel may connect the proximal end of the flexible or at least partly flexible housing to the distal end. The bypass channel is preferably formed as an integral part of the flexible or at least partly flexible housing. However, the bypass channel is expediently not in fluid communication with the interior chamber. The bypass channel, may contain a valve. The valve may be arranged at the distal end of the bypass channel. Alternatively, the valve may be arranged at the proximal end of the bypass channel. The valve may be arranged in the at least one flexible section or in a further flexible section of the housing. Preferably, the valve is a slit valve similar in design to the slit valve arranged preferably at the distal end of the interior chamber, as described above. The proximal end of the bypass channel may be not sealed with a cap. Accordingly, the bypass channel may be open to fluid flow of the first medicament held in the primary reservoir when the medicated module is attached to the injection device. A protrusion may be located on the outside surface of the bypass channel. The protrusion may be operatively connected to the bypass valve. The protrusion may be arranged closer to the distal end of the medicated module than the previously described protrusion of the flexible or at least partly flexible housing. The protrusion may be configured to mechanically cooperate with, preferably to engage with, the needle guard when the medicated module is connected to the drug delivery device. This engagement may cause the slit valve of the bypass channel to open. In this valve position, with the needle guard in an extended, e.g. distal, position and the module attached to the drug delivery device, the medicated module can be primed with the first medicament. In particular, the first medicament may flow through the bypass channel due to the opened bypass valve. As the end cap valve and the slit valve arranged at the distal end of the interior chamber are closed, the first medicament is prevented from flowing through the interior chamber of the flexible or at least partly flexible housing for priming the module.

For injection, the needle guard may be retracted into the module housing e.g. the needle guard may be moved in the proximal direction. Accordingly, the needle guard may no longer engage the protrusion on the bypass channel, thus allowing the bypass slit valve to close. As the needle guard retracts further it may mechanically cooperate with, in particular engage, the other protrusion on the flexible or at least partly flexible housing which is preferably arranged axially, in particular proximally, offset from the protrusion which the needle guard engages when the medicated module is attached to the device as described above. Accordingly, the interior chamber valve at the distal end of the flexible or at least partly flexible housing may be caused to open. Fluid communication of the primary reservoir and the reservoir of the medicated module and, thus, dispense of the second medicament contained in the flexible or at least partly flexible housing may be enabled as described above.

In particular, during retraction, e.g. movement in the proximal direction, the needle guard may engage said protrusion located on the outside of the flexible or at least partly flexible housing. This engagement may exert a force on the protrusion, which in turn may cause the flexible housing to yield or deform, thus opening the slit valve which is preferably arranged at the distal end of the flexible housing. Disengagement of the guard from the protrusion may remove the force. Accordingly, after disengagement of the needle guard and the protrusion, the flexible or at least partly flexible housing may return to its previous shape thereby causing the valve to close.

According to an embodiment, the interior chamber of the reservoir is pre-filled with the second medicament, preferably a single dose of the second medicament. The second medicament may be a liquid medicament, such as a GLP-1 or a premix of insulin and a GLP-1.

The medicated module holding the previously described reservoir may comprise a housing as described above. The housing could comprise multiple parts. Preferably, the housing comprises the two needle cannulae mounted securely in the medicated module and configured to be in fluid communication with the interior chamber during needle guard retraction. When the medicated module is first attached to the drug delivery device, the needle guard in the medicated module may be urged or biased distally causing it to engage one of the protrusions on the flexible or at least partly flexible housing of the reservoir, e.g. the protrusion arranged closer to the distal end of the flexible or at least partly flexible housing, e.g. the protrusion arranged on the outer surface of the bypass channel. Accordingly, the bypass slit valve in the bottom or distal end of the fluid bypass channel may be opened. This fluid flow path or channel may be used in the priming function of the delivery device in delivery/priming of the first/primary medicament. This bypass could be achieved by a number of means designed such that the primary medicament could flow to the dispense interface without interacting with the medicament contained within the interior chamber. Preferably, the bypass is configured as part of the flexible or at least partly flexible housing, for example, as a tube or conduit running down the outside wall of the reservoir such that the first medicament will flow from the primary reservoir through the proximal needle cannula into the bypass and then out through the slit valve and ultimately out the distal or injection needle.

Although the design of the needle guard is not critical to the present disclosure, it is preferably operably connected to the housing and configured to move in an axial direction during application to an injection site. The needle guard may function to control the opening of the slit valve for the second medicament. The retraction of the needle guard may be the distinguishing action which 'tells' the system that the user is injecting. The guard can also include a guard lock that may prevent any further use of the injection needle that is mounted in an inner housing. The design of the guard lock is not critical to the present disclosure, however, a preferred method includes the use of rotating sleeve or a moving or sliding lock contained within the module. A moving lock design may be one configured such that when the needle guard moves axially in the proximal direction it engages (picks up) the moving lock and then when the guard reverses direction (moving in the distal direction) it carries with it the moving lock. At a point when the guard has finished its reverse movement, the moving lock becomes fixed or locked to a non-moving portion of the medicated module while remaining engaged to the guard. This may prevent the guard from further axial movement in either direction. Other locking mechanisms could be used and could also allow single, double or multiple uses of the device.

A further aspect relates to a drug delivery device. The drug delivery device may comprise the previously described medicated module. The drug delivery device may comprise a primary reservoir, e.g. a cartridge. The primary reservoir may hold at least one dose, preferably a plurality of doses, of a further medicament.

Before the needle guard is retracted for the first time, the user can prime the drug delivery device using only the further, e.g. the first, medicament held in the primary reservoir, without dispensing the second medicament held in the interior of the flexible or at least partly flexible housing. In particular, when the medicated module is connected to the device and the needle guard is extended in the distal direction, the bypass valve and the needle guard may mechanically cooperate such that the bypass valve is opened for dispensing the first medicament. After priming, if the user has not already set a dose of the first medicament, the user may the set a dose of the first medicament contained in the primary reservoir of the drug delivery device using a single dose setter. When the user activates a dose button, the set dose of the first medicament from the primary reservoir may be caused to move in a distal direction and may simultaneously force substantially all of a non-user set dose (e.g. a single dose) of the second medicament from the reservoir contained in a medicated module through a single dispense interface, preferably a hollow injection needle. Upon completion of the delivery procedure, substantially all of the second medicament has been expelled as well as the selected dose of the first medicament through the single dispense interface. By "substantially all" we mean that at least about 80% of the second medicament is expelled from the drug delivery device, preferably at least about 90% is expelled. Upon completion of the injection, the needle guard may prevent a second delivery or insertion through a locking mechanism as described previously, unless the medicated module has a user activated unlock or guard lock override feature to allow a final second, or further multiple injections of only the primary medicament.

The combination of compounds as discrete units or as a mixed unit may be delivered to the body via an integral needle. This would provide a combination drug injection system that, from a user's perspective, would be achieved in a manner that very closely matches the currently available injection devices that use standard needles.

According to a preferred embodiment, a reservoir for use in a medicated module is provided, comprising a flexible housing defining an interior chamber and having a proximal end and a distal end, a rigid end cap located at the proximal end and a valve located at the distal end.

According to a preferred embodiment, a reservoir for use in a medicated module is provided, wherein the medicated module is attachable to a drug delivery device. The reservoir comprises a housing comprising at least one flexible section, the housing defining an interior chamber and having a proximal end and a distal end. The reservoir further comprises a rigid end cap located at the proximal end and a valve located in the flexible section.

According to a preferred embodiment, a medicated module is provided comprising the previously described reservoir. The medicated module is attachable to a drug delivery device, the drug delivery device comprising a primary reservoir of a first medicament, and the medicated module comprising a second medicament which is retained in the interior chamber defined by the flexible or at least partly flexible housing of the reservoir.

According to a preferred embodiment, a medicated module is provided which is attachable to a drug delivery device. The medicated module comprises a housing having a proximal end a distal end, where the proximal end has a connector configured for attachment to the drug delivery device. The medicated module comprises a reservoir in a portion of the housing, the reservoir comprising a single dose of a medicament, a flexible or at least partly housing defining an interior chamber and having a proximal end and a distal end, a rigid end cap located at the proximal end and a slit valve located at the distal end. The medicated module comprises a needle guard operably connected to the housing and configured to move in an axial direction during application to an injection site and to engage the flexible or at least partly flexible housing to open the valve.

The medicated module of our disclosure can be designed for use with any drug delivery device with an appropriate compatible interface. However, it may be preferable to design the medicated module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

The medicated module makes it expediently possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment, the primary drug delivery device is used more than once and therefore is multi-use. However, the drug delivery device may also be a single use disposable device. Such a device may or may not have a replaceable reservoir of the primary drug compound, but the present disclosure is equally applicable to both scenarios. It is also possible to have a suite of different medicated modules for various conditions that could be prescribed as one-off extra medication to patients already using a standard drug delivery device. Should the patient attempt to reuse a previously used medicated module, the locking needle guard that may be activated after drug dispense or insertion that could alert the patient to this situation. Other means of alerting the user may include some (or all) of the following:

Physical prevention of medicated module re-attachment to the primary drug deliver device once the module has been used and removed.

Physical/hydraulic prevention of subsequent liquid flow through the drug dispense interface once it has been used.

Physical locking of the dose setter and/or dose button of the primary drug delivery device.

Visual warnings (e.g. change in color and/or smell and/or warning text/indicia within an indication window on the module once insertion and/or fluid flow has occurred).

Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have cognitive or dexterity difficulties.

The present disclosure also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present disclosure will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
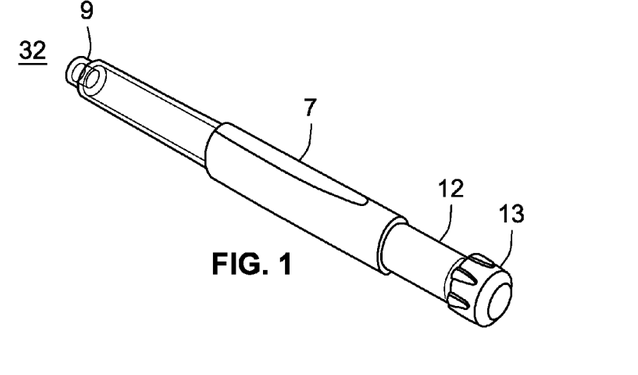
FIG. 1 illustrates one possible drug delivery device.

Specific embodiments of the disclosed medicated module enable administering a fixed predetermined dose of a second drug compound (medicament) and a variable dose of a primary or first drug compound through a single output or drug dispense interface. Setting the dose of the primary medicament by the user automatically determines the fixed dose of the second medicament, which preferably is a single dose contained in a reservoir or sealed capsule. In a preferred embodiment, the drug dispense interface is a needle cannula (hollow needle). FIG. 1 illustrates one example of a drug delivery device 7 that the medicated module 4 (see FIG. 2) can be attached to via the connection means 9 arranged at the distal end 32 of device 7. Each medicated module 4 is preferably self-contained and provided as a sealed and sterile disposable module that has an attachment means 8 compatible to the attachment means 9 at the distal end 32 of device 7. Although not shown, the medicated module 4 could be supplied by a manufacturer contained in a protective and sterile container, where the user would peel or rip open a seal on the container itself to gain access to the sterile medicated module.

In some instances, it might be desirable to provide two or more seals for each end of the medicated module 4 but any other means of sterile supply are also equally applicable and acceptable.

Figure 2:
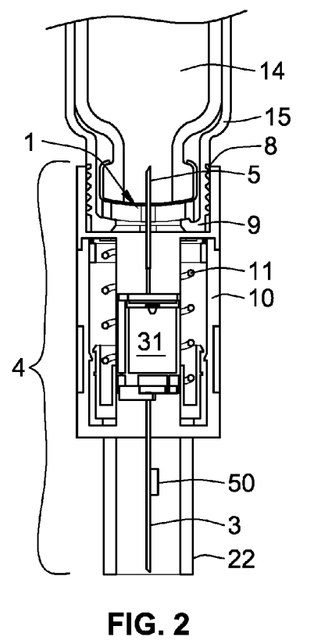
FIG. 2 illustrates a sectioned view of an embodiment of the medicated module having a flexible reservoir containing two camelback type valves.
Figure 3:
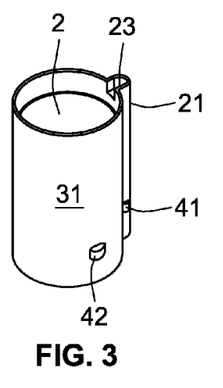
FIG. 3 illustrates a close-up perspective view of the flexible reservoir.
Figure 4:
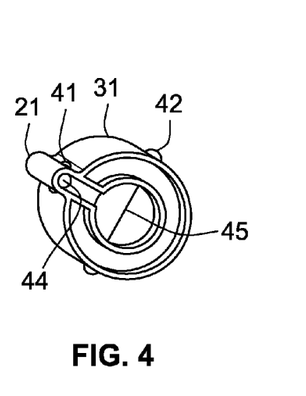
FIG. 4 illustrates a close-up perspective view of the distal end of the flexible reservoir.
Figure 5:
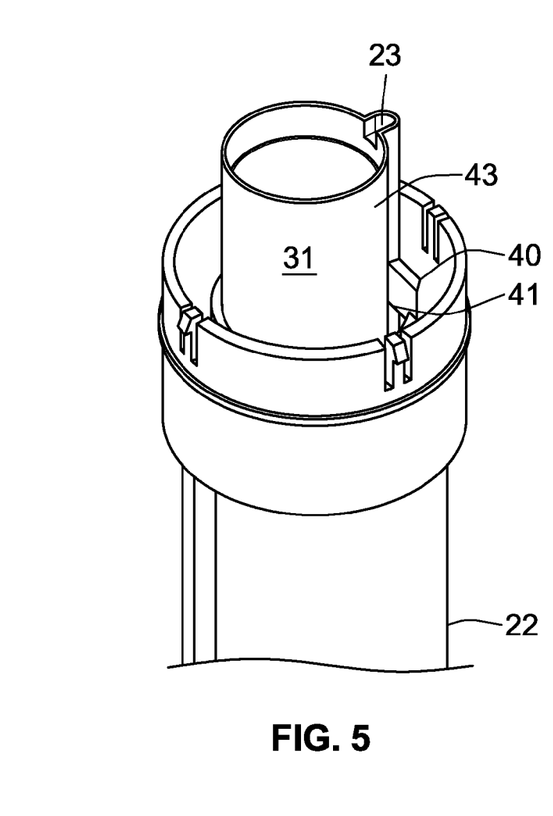
FIG. 5 illustrates a close-up perspective view of the interaction of the needle guard with the flexible reservoir, where the needle guard and reservoir are in a bypass or priming mode.

Any known attachment means 8 can be used to attach the medicated module 4 to the chosen drug delivery device 7, including all types of permanent and removable connection means, such as threads, snap locks, snap fits, luer locks, bayonet, snap rings, keyed slots, and combinations of such connections. FIG. 2 illustrates the attachment means 8 as a screw thread that would engage threads 9 of the distal end 32 of drug delivery device 7. The embodiments shown in FIGS. 2-5 have the benefit of the second medicament 2 as a single dose being contained entirely within flexible reservoir 31. Use of a flexible self-contained reservoir or capsule 31 may minimize the risk of material incompatibility between the second medicament 2 and the materials used in the construction of the medicated module 4, specifically housing 10 or any of the other parts used in the construction of the medicated module 4.

To minimize the residual volume of the second medicament 2, caused by recirculation and/or stagnant zones, that might remain in the flexible capsule/reservoir 31 at the end of the dispense operation, it is preferable to have a flow distribution system (not shown) in place or contained within the capsule 31. Preferably, the design of flow distribution system should ensure that at least about 80% of the second medicament 2 is expelled from the capsule 31 through the distal end of needle 3. Most preferably, at least about 90% should be expelled. Ideally, displacement of the first or primary medicament from the primary reservoir 14 through the capsule 31 will displace the second medicament 2 without substantial mixing of the two medicaments.

The medicated module 4 comprises two needle cannulae 3, 5. The first needle cannula 3 is arranged at the distal end of the module 4. The second needle cannula 5 is arranged proximally from the first needle cannula 3. The reservoir or capsule 31 of the medicated module is axially arranged between the needle cannulae 3, 5. The first and the second needle cannulae 3, 5 are positioned to establish fluid communication with the capsule 31.

Attachment of the medicated module 4 to the multi-use device 7 causes the engagement needle 5 located in the proximal end of the medicated module 4 to penetrate septum 1 sealing the distal end of primary reservoir or cartridge 14 of the multi-use device 7. Accordingly, the cartridge 14 is introduced in the device 7 before the module 4 is attached to the device 7. The cartridge 14 of the device 7 is filled with first medicament before it is attached to the device 7. Once the engagement needle 5 has passed through the septum 1 of the cartridge 14, fluid connection is made between the first or primary medicament and needle 5.

Prior to attaching the medicated module 4 to the drug delivery device 7, sleeve 15 is biased in a proximal direction by a biasing member, such as spring 11, which may also bias needle guard 22 into a fully extended, e.g. distal, first starting position as shown in FIG. 2. The capsule 31 of the medicated module 4 is pre-filled with secondary medicament 2 before it is attached to the device 7. When the medicated module 4 is attached to the cartridge holder or connector 9 of the drug delivery device 7, sleeve 15 is moved distally and exerts a force through spring 11 on needle guard 22. This causes needle guard 22 to move distally in such a manner that one or more protrusions 40 located on the needle guard 22, preferably on an inner surface of needle guard 22, engage one or more protrusions 41 located on the outside of the flexible housing 43 of capsule 31 (see FIG. 5). This engagement causes bypass slit valve 44 at the distal end of bypass channel 21 to squeeze open which is an effect of the flexibility of the reservoir 31, in particular of the housing 43 of the reservoir 31.

Figure 6:
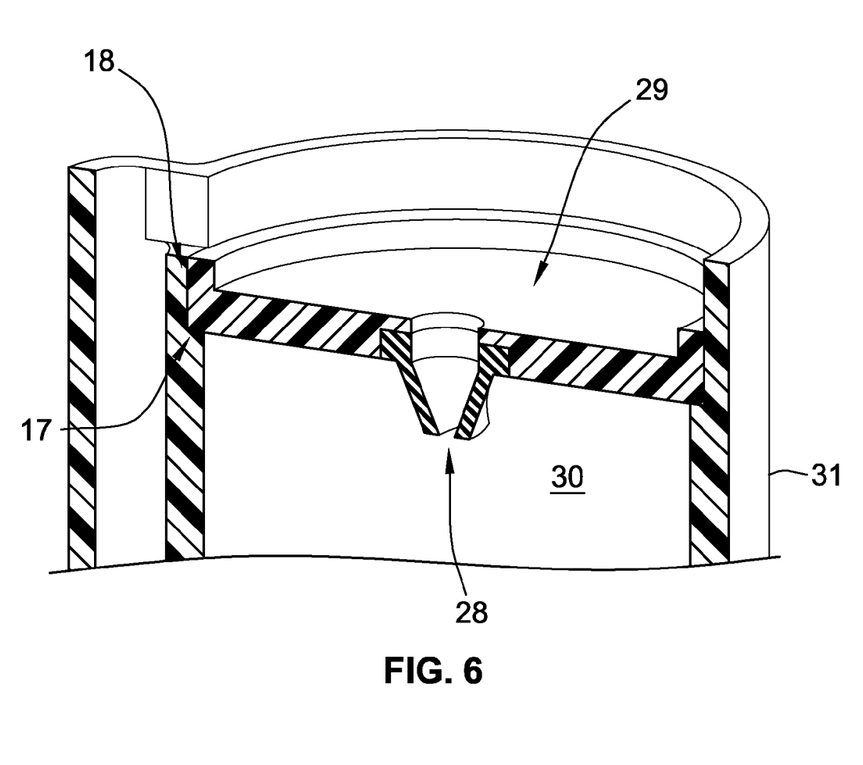
FIG. 6 illustrates a close-up sectional perspective view of the proximal end of the flexible reservoir illustrating the rigid cap member and integral duck valve.

At this point, the system can be primed by setting a small dose of primary medicament using a dose setter 12 (see FIG. 1) and pushing dose button 13. This small set dose of primary medicament will flow from reservoir 14, out through proximal needle cannula 5 and into open top 23 of bypass channel 21. The primed medicament will flow down bypass channel 21, out through open bypass slit valve 44 and be dispensed through needle cannula 3. The primed medicament does not mix with the second medicament 2 in reservoir 31 because the proximal end of the interior chamber 30 contains a rigid cap 29. The rigid cap 29 forms a liquid seal to isolate the second medicament 2 during priming. The rigid cap 29 contains a check valve (i.e. a "duck" valve) 28, which prevents flow of the primed medicament because slit valve 45 is in a closed position (see FIG. 6). Additionally, the flexible housing 43 can have a shoulder 17 that accepts rigid member 29 through an interference fit 18. The shoulder 17 can be configured to limit the insertion height of rigid member 29 into the interior chamber 30. Priming fluid flows down the bypass channel 21 as it is the channel of least resistance. There is nowhere for the fluid to flow into the interior chamber 30 as its exit is sealed.

After priming, a dose can be set in the normal manner (e.g. by dialing out the appropriate number of units or cocking the device 7 if only a single dose is possible). Dispense of the medicaments is then achieved by applying the needle guard 22 to an injection site and subcutaneously injecting the medicaments via activation of a dose button 13 on device 7. The dose button 13 can be any triggering mechanism that causes the dose of the first medicament that was set by the dose setter 12 to move towards the distal end 32 of the device 7. In a preferred embodiment, the dose button 13 is operably connected to a spindle that engages a piston in the primary reservoir 14 of the first medicament. Application to an injection site causes needle guard 22 to retract into housing 10 of the medicated module 4. The needle guard or safety shield 22 could be any design that would prevent accidental needle sticks and/or reduce the anxiety experienced by users who suffer from needle phobia. The exact design of the safety shield is not critical to the present disclosure, however, a preferred design, as disclosed below, is one that allows only a single use of needle 3 unless the medicated module 4 is configured with a user override button to unlock the needle guard 22 for a second or multiple further injection(s).

Retraction of the needle guard 22 causes one or more protrusions 50 on the needle guard 22 to engage one or more protrusions 42 on the flexible housing 43 of capsule 31. This engagement causes slit valve 45 to squeeze open, which is enabled by the flexibility of the housing 43, allowing the second medicament 2 to flow out of the interior chamber 30 and be dispensed through output needle 3. Once slit valve 45 is opened, the hydraulic pressure within the capsule 31 is reduced on the distal portion of check valve 28. The pressure of the primary medicament exerting on the proximal side of rigid member or end cap 29 and the proximal portion of check valve 28 will cause the check valve 28 be forced open allowing the set dose of primary medicament to flow into the interior chamber 30 of capsule 31, thus driving or forcing out the second medicament 2. In some instances, it may be desirable to have a check valve 28 on the entrance to the bypass channel 21, too. This would allow fluid flow to be regulated by the opening of slit valves 44, 45 at the end of the bypass channel 21 or the end of the interior chamber 30. This would alleviate concerns that when the needle guard 22 is up, the fluid first fills the bypass channel 21 before exerting a force on the rigid member 29.

In any of the above described embodiments, the second medicament 2 may be either in a powdered solid state, any fluid state contained within the secondary reservoir or capsule 31, or coated to the inside surface of the drug dispense interface. The greater concentration of the solid form of the medicament 2 has the benefit of occupying a smaller volume than the liquid having lower concentration. This in turn reduces the ullage of the medicated module 4. An additional benefit is that the solid form of the second medicament 2 is potentially more straightforward to seal in the secondary reservoir 31 than a liquid form of the medicament 2. The device 7 would be used in the same manner as the preferred embodiment with the second medicament 2 being dissolved by the first medicament during dispense.

To minimize diffusion of the second medicament 2 contained in the reservoir capsule 31 within the medicated module 4 into the primary medicament during dispense of the medicaments a flow distribution system may be used. Such a system also ensures efficient expulsion of the second medicament 2 from the system and greatly minimizes residual volume. One possible embodiment of a flow distribution system would be a flow distributor configured as an annular pin that is positioned in capsule 31 and configured such that the second medicament 2 fills flow channels that are defined by the shape and location of two or more support ribs. The flow distributor (annular pin) can be constructed of any material that is compatible to the primary/first and second medicaments. A preferred material would be that typically used to manufacture septa or pistons (bungs) found in multi-dose medicament cartridges, although any material that is compatible with the medicament during long term storage would be equally applicable. The shape of the flow channels can be optimized for a plug flow of medicament by varying the dimensions and number of support ribs. The cross-sectional area of the annulus formed between the flow distributor and the wall of the vial should be kept relatively small. The volume available to store the second medicament 2 would equal the internal volume of the capsule 31 minus the volume of the flow distributor. Therefore, if the volume of the flow distributor is marginally smaller than the internal volume of the capsule 31, a small volume is left which the second medicament 2 occupies. Hence, the scale of both the capsule 31 and the flow distributor can be large while storing a small volume of medicament 2. A further benefit of this is that as the available volume for medicament 2 is defined by the difference in volumes between the flow distributor and its housing, the external capsule geometry is not dictated by the volume of medicament 2. Resultantly for small volumes of second medicament 2 (e.g. 50 micro liters), the capsule 31 can be of an acceptable size for handling, transport, manufacture, filling and assembly.

The connection or attachment between the drug delivery device 7 and the medicated module 4 of the above described embodiments may contain additional features (not shown), such as connectors, stops, splines, ribs, grooves, and the like design features, that ensure that specific medicated modules 4 are attachable only to matching drug delivery devices 7. Such additional features would prevent the insertion of a non-appropriate medicated module 4 to a non-matching injection device.

The shape of the medicated module 4 may be a cylindrical body or any other geometric shape suitable for defining a fluid reservoir or for containing discrete self-contained reservoir 31 of the second medicament 2 and for attaching one or more needle cannula 3, 5. The medicated module 4 can be manufactured from glass or other drug contact suitable material. The integrated injection needle 3 can be any needle cannula suitable for subcutaneous or intramuscular injection.

Preferably, the medicated module 4 is provided by a drug manufacturer as a stand-alone and separate device that is sealed to preserve sterility. The sterile seal of the medicated module 4 is preferably designed to be opened automatically, e.g. by cutting, tearing or peeling, when the medicated module 4 is advanced or attached to the drug delivery device 7 by the user. Features such as angled surfaces on the end of the injection device 7 or features inside the medicated module 4 may assist this opening of the seal.

The medicated module 4 should be designed to operate in conjunction with a multiple use injection device 7, preferably a pen-type multi-dose injection device, similar to what is illustrated in FIG. 1. The injection device 7 could be a reusable or disposable device. By disposable device it is meant an injection device 7 that is obtained from the manufacturer preloaded with medicament and cannot be reloaded with new medicament after the initial medicament is exhausted. The device 7 may be a fixed dose or a settable dose and preferably a multi-dose device, however, in some cases it may be beneficial to use a single dose, disposable device.

A typical injection device 7 contains a cartridge or other reservoir 14 of medication. This cartridge 14 is typically cylindrical in shape and is usually manufactured in glass. The cartridge 14 is sealed at one end with a rubber bung and at the other end by a rubber septum. The injection device is designed to deliver multiple injections. The injection device may further comprise a dose setter; the dose setter may be operably connected to the delivery mechanism. The injection device comprises a dose button; the dose button may be operably connected to the delivery mechanism. The dose button may be any triggering mechanism that causes the dose of the medicament that was set by the dose setter to move distally towards the distal end of the device. In a preferred embodiment, the dose button is operably connected to a spindle that engages a piston in the primary reservoir of the first medicament. In a further embodiment the spindle is a rotatable piston rod comprising two distinct threads. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

REFERENCE NUMERALS

1 Septum
2 Second medicament
3 Needle
4 Medicated module
5 Engagement needle
7 Drug delivery device
8 Attachment means
9 Connection means
10 Housing
11 Spring
12 Dose setter
13 Dose button
14 Primary reservoir/cartridge
15 Sleeve 17 Shoulder
18 Interference fit
21 Bypass channel
22 Needle guard
23 Open top
28 Check valve
29 Cap
30 Interior chamber
31 Flexible reservoir/capsule
32 Distal end
40 Protrusion
41 Protrusion
42 Protrusion
43 Flexible housing
44 Bypass slit valve
45 Slit valve
50 Protrusion

We claim:

1. A medicated module attachable to a drug delivery device—and comprising a second medicament, the drug delivery device comprising a primary reservoir of a first medicament, wherein the medicated module further comprises
a proximal needle cannula and a distal needle cannula,
a reservoir,
a needle guard adapted and arranged to provide protection against the distal needle cannula and configured to move in an axial direction during application to an injection site,
the distal end of the distal needle cannula being configured for being applied to an injection site and a proximal end of the proximal needle being configured for piercing the primary reservoir,
wherein the reservoir is arranged in the axial direction between the distal and the proximal needle cannula, the proximal needle cannula and the distal needle cannula configured to be in fluid communication with the reservoir when the needle guard is moved in a proximal direction, wherein the reservoir comprises:
a housing comprising a flexible section, the housing defining an interior chamber, having a proximal end and a distal end and retaining said second medicament; and
a distal valve located in the flexible section and at the distal end of the housing, wherein when the needle guard is moved in the proximal direction, the distal valve is forced to an open position due to mechanical cooperation of the at least one flexible section and the needle guard such that the second medicament is allowed to flow out of the interior chamber and be dispensed through the distal needle cannula.

2. The medicated module of claim 1, where the housing comprises a medical grade of silicon or thermoplastic elastomers.

3. The medicated module of claim 1, where the distal valve is a slit valve.

4. The medicated module of claim 1, where the housing comprises a bypass channel, wherein the bypass channel connects the proximal end to the distal end and is not in fluid communication with the interior chamber.

5. The medicated module of claim 4, where the bypass channel comprises at least one slit valve.

6. The medicated module of claim 5, where the housing comprises at least two protrusions, where each protrusion is operably connected to one of the valves, and where each protrusion is configured to engage with the needle guard when the medicated module is connected to the drug delivery device such that opening of the respective valve is enabled.

7. The medicated module of claim 5, where the bypass channel is opened to fluid flow of the first medicament from the primary reservoir when the medicated module is attached to the drug delivery device.

8. The medicated module of claim 4, wherein the at least one slit valve of the bypass channel is located in the flexible section or in a further flexible section of the housing.

9. The medicated module of claim 1, where the housing comprises a protrusion that is operably connected to the distal valve and that is configured such that mechanical cooperation of the protrusion and a member of a drug delivery device enables opening of the distal valve.

10. The medicated module of claim 1, wherein at the proximal end of the housing a rigid end cap is located, wherein the end cap comprises a check valve which is adapted and arranged for enabling fluid communication with the interior chamber.

11. The medicated module of claim 1, comprising a housing configured for attachment to the drug delivery device, wherein the needle guard is operably connected to the housing.

12. The medicated module of claim 11, wherein mechanical cooperation of the housing and the needle guard enables opening of the respective valve of the reservoir.

13. The medicated module of claim 1, where the housing of the medicated module comprises a bypass channel, wherein the bypass channel connects the proximal end to the distal end and is not in fluid communication with the interior chamber, where the bypass channel comprises at least one slit valve, where the housing comprises at least two protrusions, where each protrusion is operably connected to one of the valves and, wherein the respective protrusion is configured to engage the needle guard when the needle guard is in two different axial positions.

14. A drug delivery device comprising the medicated module according to claim 1.

15. The drug delivery device of claim 14, wherein the housing of the medicated module comprises a bypass channel, wherein the bypass channel connects the proximal end to the distal end and is not in fluid communication with the interior chamber, where the bypass channel comprises a slit valve, wherein the housing is configured to mechanically cooperate with the needle guard when the medicated module is connected to the drug delivery device and the needle guard is extended in a distal direction such that the slit valve of the bypass channel is opened.

16. The drug delivery device of claim 14, wherein the housing is configured to mechanically cooperate with the needle guard when the needle guard is retracted in a proximal direction such that the valve of the housing is opened and such that fluid communication of the primary reservoir and the reservoir of the medicated module is enabled.

17. The drug delivery device of claim 14, wherein the distal end of the drug delivery device has first attachment means and the medicated module has second attachment means at the proximal end of the housing.

* * * * *